(12) United States Patent
Sedoglavich et al.

(10) Patent No.: US 8,705,031 B2
(45) Date of Patent: Apr. 22, 2014

(54) PARTICLE SORTING APPARATUS AND METHOD

(75) Inventors: Nemanya Sedoglavich, Boston, MA (US); Stuart Buddy Ehrlich, Boston, MA (US); Emanuel Tito Mendes Machado, Merrimack, NH (US); Johnathan Charles Sharpe, Hamilton (NZ)

(73) Assignee: Cytonome/ST, LLC, Boston, MA (US)

( * ) Notice: Subject to any disclaimer, the term of this patent is extended or adjusted under 35 U.S.C. 154(b) by 0 days.

(21) Appl. No.: 13/363,112

(22) Filed: Jan. 31, 2012

(65) Prior Publication Data

US 2012/0202237 A1   Aug. 9, 2012

Related U.S. Application Data

(60) Provisional application No. 61/439,757, filed on Feb. 4, 2011.

(51) Int. Cl.
*G01N 21/00* (2006.01)
(52) U.S. Cl.
USPC ............................................ 356/337; 356/338
(58) Field of Classification Search
CPC ............................ G01N 21/00; G01N 21/0205
See application file for complete search history.

(56) References Cited

U.S. PATENT DOCUMENTS

| 5,831,723 | A | 11/1998 | Kubota |
| 5,998,212 | A | 12/1999 | Corio et al. |
| 6,372,506 | B1 | 4/2002 | Norton |
| 2006/0263829 | A1 | 11/2006 | Evans |
| 2007/0195310 | A1 | 8/2007 | Kanda |
| 2009/0248317 | A1 | 10/2009 | Nagai |

OTHER PUBLICATIONS

PCT International Search Report and Written Opinion dated Apr. 27, 2012 issued in related PCT Application No. PCT/US2012/023247 (11 pages).
Verwer, Ben, BD FACSDiVa Option, 2002.

*Primary Examiner* — Michael P Stafira
(74) *Attorney, Agent, or Firm* — McCarter & English, LLP; David R. Burns (57) ABSTRACT

A particle analyzing and/or sorting apparatus and the associated methods. One aspect of the described embodiments relates to an analyzer, or a sorter, having acquisition and sort electronics in the form of a field programmable gate array for processing detected signals. Another aspect relates to a droplet based approach of analyzing and sorting particles and may further include a dynamic element, such a dynamic drop delay. In still another broad aspect, an apparatus and method for dynamically varying other sorting parameters.

30 Claims, 5 Drawing Sheets

PARTICLE SORTING APPARATUS AND METHOD

This application claims the benefit of U.S. Provisional Patent Application 61/439,757, filed on Feb. 4, 2011, the entire text of which is incorporated herein by reference.

This application is related to International Patent Cooperation Treaty Application No. PCT/US12/23247, filed on Jan. 31, 2012, entitled "Particle Sorting Apparatus and Method."

FIELD

The present disclosure generally relates to a particle sorting apparatus and associated methods for sorting particles, and more particularly relates to methods and systems for controlling, operating and optimizing flow cytometers for enriching populations of particles.

BACKGROUND

Various flow cytometers and microfluidic systems exist for the purposes of analyzing and separating particles. Each of these instruments has various disadvantages making them less desirable for certain applications. Early flow cytometers were able to count particles in fluid streams and were eventually able to differentiate and count particles having different characteristics, such as different sizes. As new dyes and staining procedures developed, the capacity of flow cytometers to differentiate particle characteristics improved, resulting in a variety of cytometers and techniques for analyzing cells according to their shape, density, size, DNA content, and DNA sequence among other features. The DNA content of a cell can be used to determine a cell cycle, the presence of cancer or, in the case of sperm, can be used to differentiate X-chromosome bearing sperm cells from Y-chromosome bearing sperm cells. These older systems operated with analog acquisition and sort electronics that are unable to differentiate particles within a certain proximity resulting in a large number of particles which could not be analyzed or sorted.

With the introduction of digital signal acquisition and digital signal processing, flow cytometers were able to evaluate increasing numbers of particles per second and make more complex multiple parameter analysis. Ellison et al. (WO 01/28700) describe a multiple digital signal processor configuration for performing operations, such as translations, in parallel with a first digital signal processor. Similarly, Durack et al. (WO 04/088283) describe a sorter with four digital signal processors for acquiring and processing flow cytometer signals to sort particles. Each of Durack et al. and Ellison et al. depend upon a triggering event, after which coincidences are determined and the drop delay is applied to the events in a FIFO manner for sorting. Even in flow cytometers dividing tasks among four digital signal processors capable of operating independently and in parallel, when enough particles are detected in rapid succession it is possible for the system to bottleneck, requiring incoming data representing particle events to be cued. After a certain cue is reached, events are aborted to save processing time. Such bottlenecks and aborts may result in erroneous sort decisions. Each digital signal processor is capable of performing a single task at a time and requires some number of clock cycles to achieve each task. The complex computations required for classifying events and sorting particles at event rates exceeding 40,000 per second can surpass the number of clock cycles four parallel digital signal processors can perform. Therefore, a need exists for a robust methodology and apparatus for precisely tracking parameters surrounding each individual particle and each expected droplet and for executing accurate sort decisions.

A common flow cytometer for sorting is the jet-in-air flow cytometer, such as the one described by Hoffman et al. (WO 01/29538). The jet-in air flow cytometer focuses particles within a fluid stream for analysis and perturbs the fluid stream with an oscillator for separating particles. Perturbing the fluid stream results in the formation of droplets downstream of an inspection zone, at which the particles are interrogated and analyzed. In order to sort particles within the fluid stream, the fluid stream may be charged just before a forming droplet, including the particle of interest, separates at a break off point. The droplet retains the charge and as it passes through an electromagnetic field downstream of the break off point is directed to the desired location.

A precise coordination of the droplet charge signal to the break off of the droplet containing the particle to be sorted is required. Historically, this coordination required empirical, iterative procedures to first determine the drop delay within a period of the drop drive frequency, and then within a fraction of the drop drive frequency. Later, automated systems would appear for calculating the drop delay, such as described in United States Patent Application Publication 2011/0221892 (Neckels et al.). Each of these systems have certain disadvantages associated with previously unrecognized problems associated with particle locations in a droplet effecting the correct window for charging said droplet. This historically static parameter is one of the most important determinations required for performing accurate sort actions. Accordingly, a need exists for an improved method and system for sorting particles, especially for particles which can affect operational parameters of a jet-in-air flow cytometer, such as the drop delay.

SUMMARY OF INVENTION

Certain aspects of this disclosure relate to an improved system and method for analyzing, classifying and sorting particles. The provisions of such a system, in one embodiment include: a particle delivery device for delivering particles to an inspection zone; an electromagnetic radiation source for interrogating particles at the inspection zone; a detection system for producing at least one signal based upon electromagnetic radiation emitted from or reflected from the interrogated particles; a processing unit with a field programmable gate array in communication with the detection system, the field programmable gate array including instructions for determining event parameters from the at least one signal, instructions for classifying particles, and instructions for applying a sort logic to make a sort decision; and a separator for sorting particles according to the corresponding sort decisions.

One aspect of this disclosure provides for the system having acquisition and sort electronics in the form of an FPGA interfaced via a PCIe board installed on a desktop personal computer (PC) or on a laptop. In this way, the acquisition and sort electronics can share a common bus with the graphic user interface of the PC. Whereas previously jet-in-air flow cytometers comprised either a rack of electronics including analog acquisition and sort electronics or large boards containing multiple digital signal processors, certain aspects of this disclosure relate to sort and acquisition electronics which are capable of the high speed sorting of systems having multiple digital signal processors, but are compact enough for integration into a standard desk top PC. Alternatively, a laptop computer with an external PCIe interface may also be used. In an alternative aspect, embodiments described herein may relate to an analyzer employing the same pulse detection and discrimination features employed on a field programmable gate array, but without mechanism for forming droplets or for sorting.

Another aspect of this disclosure relates to improved systems and methods for sorting with a droplet based approach. Such an approach may be achieved by generating an event memory map, having event windows corresponding to the expected formation of droplets for sorting particles. An event memory map may be compiled in the random access memory (RAM) of an FPGA for tracking information relating to each event representing a particle as well as for tracking events and parameters relating to each expected droplet. In one aspect, the event memory map provides a compilation of event parameters associated with the formation of droplets. Event parameters for each droplet can include the number of particles in a droplet, the location of particles in a droplet, the classifications of particles within a droplet, and other information about droplets and particles. Sort decisions can be made from a sort logic compiled on state machines in response to the event parameters of expected droplets and the surrounding droplets as stored in the event memory map.

One aspect of the disclosure relates to the improved system and method including instructions for, or the step of, dynamically modifying operational parameters of a sorter based upon event parameters stored in the event memory map. As one non-limiting example, the drop delay can be modified for individual droplets which have particles located close to a tail end of the droplet. The amplitude, duration, or even shape of the charge signal applied to a fluid stream for sorting may also be modified for individual expected droplets based upon the associated event parameters. Other operational parameters may include the shape, frequency, phase, or amplitude, of the drop drive signal produced for forming droplets, pressures for the sample or sheath fluid, and even the sort modes. These operational parameters may be modified based upon cumulative statistics or based on statistical sampling of any of the event parameters. As another non-limiting example, the sample pressure may be changed in order to increase or decrease the number of droplets containing more than one particle.

Certain aspects of this disclosure relate to an improved system and method for analyzing, classifying and sorting particles with a droplet based approach. The provisions of such a method include the steps of, generating an event memory map having event windows; delivering a fluid stream containing particles to an inspection zone and interrogating the particles at the inspection zone with a source of electromagnetic radiation, wherein interrogated particles produce emitted or reflected electromagnetic radiation; detecting the emitted or reflected electromagnetic radiation of the interrogated particles, and producing at least one signal containing pulses representative of the interrogated particle characteristics; comparing the at least one signal to a trigger threshold to determine the occurrence of a particle event; coordinating each particle event to an event window in the event memory map; determining measured pulse parameters for each particle event; classifying particles based upon the measured pulse parameters; determining event parameters for each event window; applying a sort logic to make a sort decision based upon the event parameters and particle classifications associated with each event window; sorting particles within each event window according to the respective sort decisions; and collecting at least one population of sorted particles.

One aspect of the droplet based approach relates to a method and apparatus which compile an event memory map during the sorting process. The event memory map can include information about each detected pulse corresponding to a particle and about each expected droplet, regardless of whether or not the droplet and its neighboring droplets contain particles. In this manner, certain aspects provided herein result in a more precise tracking of all events and all droplets. The event parameters associated with event windows in the event memory map can be used as previously described for making real time adjustments to operational sorting parameters, or can be provided as input in mathematical models for making sort decisions. Mathematical models can include models for predicting probabilities relating to classification, probabilities regarding which droplet a particle will end up in, projected purities, or other relevant information. The event memory map provides a tool for clearer logic with improved interpretation for more accurate sort systems achieved through the structured tracking of variables. As an example, the event memory map can record event parameters for surrounding expected droplets and apply a sort logic accounting for both the droplet before the current droplet and the droplet after the current droplet.

Another aspect of the droplet based approach relates to a method and apparatus having a clear concise logic implemented on a single field programmable gate array (FPGA) for better interpretation and for more accurate sort actions. A single FPGA may be programmed to perform thousands of tasks in parallel. This configuration may provide an acquisition and sort processor which is always ready to except the next event, effectively eliminating the need for cueing created by the limitations of parallel digital signal processors. For example, an FPGA may be programmed with instructions for detecting a pulse indicating the presence of a particle in a fluid stream, and for calculating measured pulse parameters of the pulse. Further instructions on the field programmable gate array may include instructions for classifying particles based on the measured pulse parameters as well as instructions determining event parameters relating to a droplet in which the pulse is expected to be sorted. The field programmable gate array can also include instructions for applying a sort logic based on the event parameters associated with the expected droplet, and based upon the classifications of all pulses within the expected droplet.

An object of this disclosure can be to provide an apparatus and method for performing more accurate sort actions. Specifically, one broad object of the methods and systems provided herein provides an apparatus and method capable of processing each detected event without cueing to prevent aborting events based on processing capacity.

Another broad object provided herein may be to track each event and to track parameters surrounding each droplet, regardless of whether or not an event is associated with each droplet.

Yet another object of this disclosure can be to provide a system and apparatus for dynamically modifying operational parameters related to sorting to improve sort accuracy.

A broad object of this disclosure can be to provide an apparatus for sorting particles and a method of sorting particles which meets the needs described above. Naturally, further objects of the disclosure are provided throughout the specification.

MODES FOR CARRYING OUT THE INVENTION

The embodiments described herein relate to the analysis and sorting of particles, such as by flow cytometry. A number of inventive concepts provided below may be combined or applied to sorting systems other than flow cytometers.

Particle Sorting System

Figure 1:
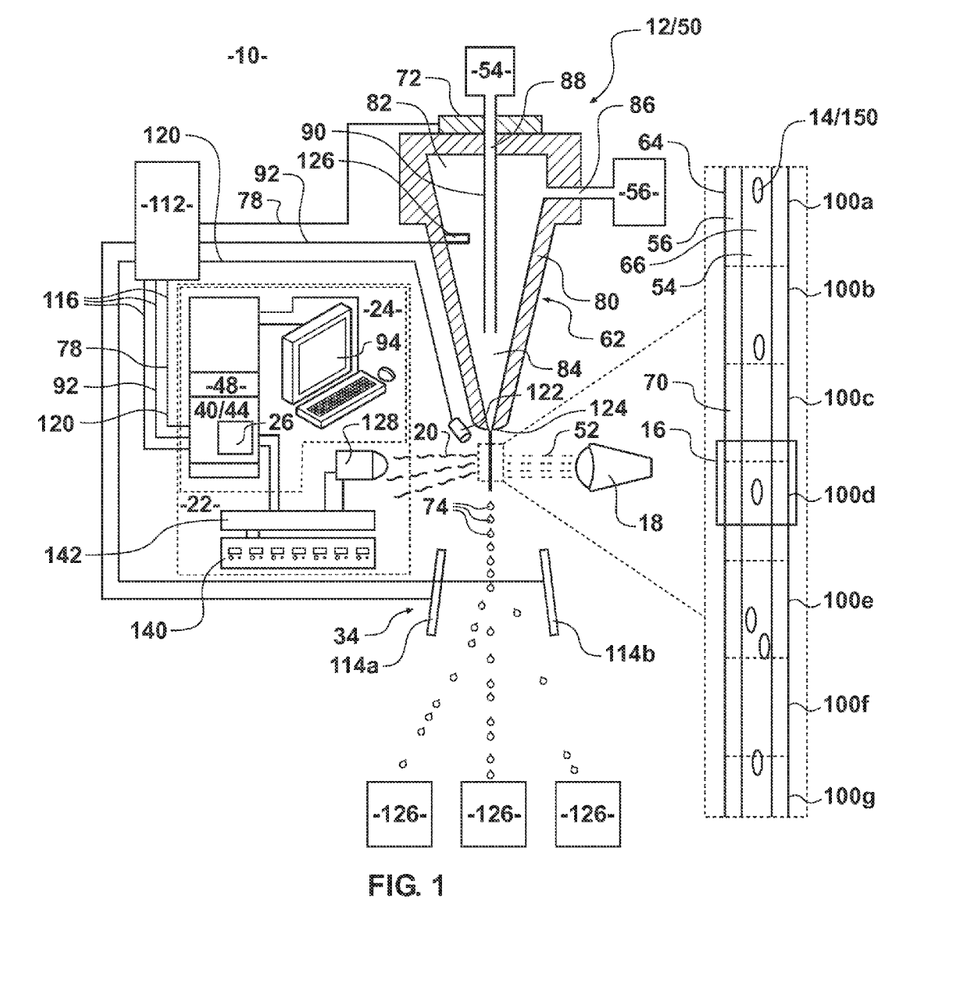
FIG. 1 illustrates a flow cytometer with acquisition and sort electronics installed on a PCIe board in accordance with certain aspects of this disclosure.

Now referring primarily to FIG. 1, an example of a particle sorting system 10 is illustrated as a jet-in-air flow cytometer. The particle sorting system 10 may include a particle delivery device 12 in the form of a jet-in-air flow cytometer sort head 50, sometimes referred to as a sort head, for delivering particles 14 to a detection system 22 and then to a separator 34.

The particles 14 may be single cell organisms such as bacteria or individual cells in a fluid, such as various blood cells, sperm or nuclei derived from tissue. Depending on the application, the particles 14 may be stained with a variety of stains, probes, or markers selected to differentiate particles or particle characteristics. Some stains or markers will only bind to particular structures, while others, such as DNA/RNA dyes, may bind stoichiometrically to nuclear DNA or RNA. Particles 14 may be stained with a fluorescent dye which emits fluorescence in response to an excitation source. As one non-limiting example, sperm may be stained with Hoechst 33342 which stoichiometrically binds to X-chromosomes and Y-chromosomes. U.S. Pat. No. 5,135,759 (Johnson et al.) and U.S. Pat. No. 7,758,811 (Durack et al.) describe methods for staining sperm, and are each incorporated herein by reference. In oriented sperm, the relative quantity of Hoechst 33342 can be determined providing means for differentiating X-chromosome bearing sperm from Y-chromosome bearing sperm. Additionally, certain embodiments are envisions to work with sequence DNA sequence specific dyes and sex specific dyes.

The sort head 50 may provide a means for delivering particles 14 to the detection system 22 and more specifically to the inspection zone 16. Other particle delivery devices 12 are contemplated for use here in, such as fluidic channels. The sort head 50 may include a nozzle assembly 62 for forming a fluid stream 64. The fluid stream 64 may be a coaxial fluid stream 64 having an inner stream 66, referred to as a core stream, containing a sample 54, and an outer stream 70 comprising sheath fluid 56. The sample 54 may include the cells or particles of interest, as well as, biological fluids, and other extenders or components for preserving cells in vivo. The sample 54 may be connected to the nozzle assembly 62 through a sample inlet 88 into a nozzle body 80 having an upstream end 82 and a downstream end 84. An injection needle 90 may be in fluid communication with the sample inlet 88 for delivering the inner stream 66 of the sample 54 centrally within the nozzle body 80 towards the downstream end 84. The sheath fluid 56 may be supplied through a sheath inlet 86 at the upstream end 82 of the nozzle body 80. The sheath fluid 56 may form an outer stream 70 which serves to hydrodynamically focused an inner stream 66 of sample 54 towards the downstream end 84 of the nozzle body 80.

In addition to the formation of the fluid stream 64, the nozzle assembly 62 may serve to orient particles 14 in the sample 54. The interior geometry of the nozzle body 80, in combination with an orienting tip 124, may subject particles, such as aspherical particles, to forces tending to bring them into similar orientations. Examples of interior nozzle body geometries for orienting particles are described in U.S. Pat. Nos. 6,263,745 6,784,768, both to Buchanan et al., each of which are incorporated herein by reference. The teachings of this disclosure are also contemplated for use with flow cytometers or other devices configured without orienting means, such as a conventional jet-in-air flow cytometers, or immersion lens flow cytometers, or such as a device described in U.S. Pat. No. 6,819,411, having radial collection or radial illumination means.

In order to perform the function of separating particles, the nozzle assembly 62 may further include an oscillator 72 for breaking the fluid stream 64 into droplets 74 down steam of the inspection zone 16. The oscillator 72 may include a piezo-electric crystal which perturbs the fluid stream 64 predictably in response to a drop drive signal 78. In FIG. 1, the drop drive signal 78 is represented by the electrical connection to the oscillator 72 carrying the drop drive signal 78. The waveform shape, phase, amplitude, and frequency of the drop drive signal may directly affect the shape and size of the droplets as well as the presence of satellites. The amplitude, shape, phase, or frequency of the drop drive signal 78 may be modified during sorting in response various operational parameters or event parameters.

FIG. 1 provides an enlarged view of the fluid stream 64 including the inner stream and 66 and the outer stream 70. The fluid stream 64 is illustrated in segments representing expected droplets 100($a$-$g$) containing particles 14, which may be sperm cells 150. The dimensions of any of the inner stream 66, outer stream 70, expected droplets 100, or particles 14 may not be illustrated to scale. The length of the fluid stream included in each expected droplet 100 depends on the frequency of the drop drive signal 78. Similarly, the widths of the inner stream 66 and the outer stream 70 may be determined by the pressure at which sample 54 and sheath fluid are supplied to the nozzle body 80, respectively. An expected droplet 100$d$ is illustrated substantially at the inspection zone 16 containing a particle 14 delivered by the particle delivery device 12 for inspection. Three additional expected droplets 100$a$, 100$b$, 100$g$ are also illustrated containing single particles, while one expected droplet 100$e$ is illustrated containing two particles, and two other expected droplets 100$c$, 100$f$ are illustrated as empty.

Once a particle 14, such as a stained particle, is delivered to the inspection zone 16, it may be interrogated with an electromagnetic radiation source 18. The electromagnetic radiation source 18 may be an arc lamp or a laser. As one non-limiting example, the electromagnetic radiation source 18 may be a pulsed laser emitting photons of radiation 52 at specified wavelengths. The wavelength of a pulsed laser may be selected based upon the particle characteristic of interest and may be selected to match an excitation wavelength of any stain or marker used to differentiate that characteristic. As a non-limiting example, a family of UV excitable dyes may be interrogated with a pulsed Vanguard Laser available from Newport Spectra-Physics and may have an emission wavelength of 355 nm and be operated at 175 mW.

Particles 14 at the inspection zone 16 may produce a secondary electromagnetic radiation in the form of emitted (fluoresced) or reflected (scattered) electromagnetic radiation 20 in response to the laser interrogation. The characteristics of the emitted or reflected electromagnetic radiation 20 may provide information relating to the characteristics of particles 14. The intensity of the emitted or reflected electromagnetic radiation 20 may be quantified in a plurality of directions and/or at a plurality of specified wavelengths to provide a large amount of information about the interrogated particles.

FIG. 1 illustrates detection system 22 comprising a first detector 128, sometimes referred to as at least one detector, configured to detect emitted or reflected electromagnetic radiation 20 from particles 14 in the inspection zone 16. The detection system 22 may comprise any number of detectors configured in one or more direction from the inspection zone 16. The first detector 128 and any additional detectors communicate signals to the processing unit 24 for differentiating particles and determining sort actions. As a non-limiting example, the first detector 128 may be configured in the forward direction, or in the same direction photons are propagated from the electromagnetic radiation source 18 toward the inspection zone 16. The first detector 128 may be a forward fluorescence detector including a filter for blocking any electromagnetic radiation below a certain wavelength. A plurality of detectors may be placed in a plurality of directions, including the rear, forward and/or side directions. Each direction may include an optical configuration of collection lenses, reflective elements, or objective lenses in combination with splitters, dichroic mirrors, filters and other optical elements for detecting the intensities of various wavelengths collected from any particular direction. Optical configurations may also be employed for detecting light extinction or light scatter.

Figure 2:
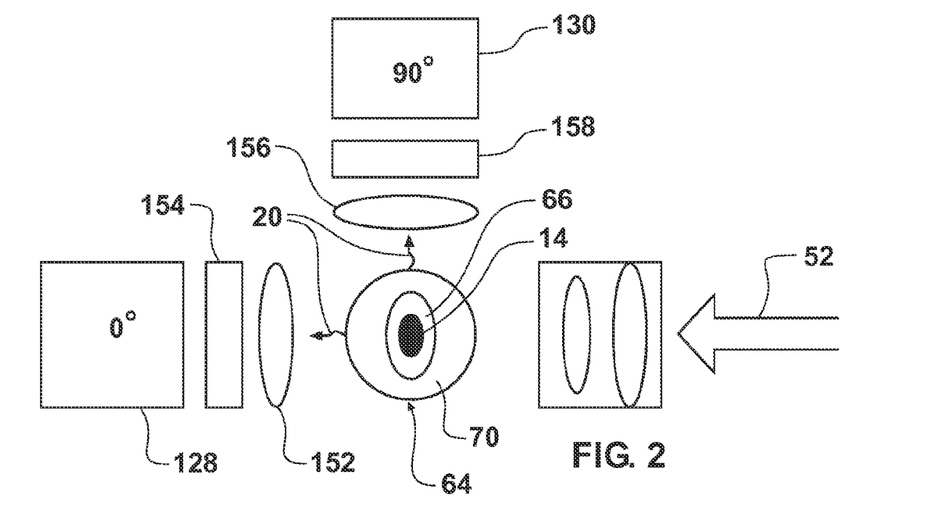
FIG. 2 illustrates a top view of certain aspects to the flow cytometer in FIG. 1.

Referring briefly to FIG. 2, an example of a detector system 22 is illustrated from an overhead view. The first detector 128 may be aligned with the photons of radiation 52 emitted by an electromagnetic radiation source 18 which may be considered the forward direction or at 0°. In one embodiment, the first detector 128 may be a photomultipler tube (PMT) for producing electrical signals quantatively representative of the intensity of the emitted or reflected electromagnetic radiation 20 incident upon the first detector 128. Exemplary photomultiplier tubes are available from Hamamtsu Corporation.

An objective 152 located in the first direction may be focused to collect emitted or reflected electromagnetic radiation 20 in the first direction. Other light collection lenses or elements are also contemplated for use with the described system. A filter 154 in line with the objective lens 152 may be selected to exclude the photons of radiation 52 emitted by the electromagnetic radiation source 18. Other optical elements may also be employed for directing emitted or reflected electromagnetic radiation 20, including dichroic mirrors, low pass filters, high pass filters, band pass filters, and pellicle filters. As one example, the filter 129 may exclude light having a wavelength less than 420 nm allowing the first detector 128 to produce an electrical output proportional to the amount of fluoresced light incident upon the first detector 128. Alternatively, the filter 154 may comprise a band pass filter for collecting light of a particular wavelength.

A second detector 130 may be placed in a second direction. As an example, the second detector 130 may be placed in the side direction (roughly orthogonal to the first detector for collecting side fluorescence) at an angle of 90° relative to the propagation of photons of radiation 52. The second detector 130 may include an objective lens 156 for focusing electromagnetic radiation in the second direction incident upon a PMT, as well as a filter 158 for blocking certain wavelengths of electromagnetic radiation. The first detector 128 and the second detector 130 may be placed in any direction, and it may be arbitrary which detector is referred to as the first detector 128 and which is referred to as the second detector 130.

Still referring to FIG. 2, a particle 14 can be seen in the inner stream 66 of the fluid stream 64. The particle 14 is illustrated with a broad flat side and a more narrow side. An example of such aspherical particles may be red blood cells or sperm cells. Depending on the characteristics of interest, such particles 14 may be generally oriented as they head into the inspection zone 16 so that the flat surface is uniformly presented to one of the two detectors and the narrow edge is uniformly presented to the other detector.

Returning to FIG. 1, each detector 128 may be controlled with a PMT controller 140 for adjusting the gain in each detector 128. Signals produced by each detector may be amplified at the detector preamplifier 142 before being passed to the processing unit 24. Depending on the particle characteristics of interest, sensors other than PMTs may be employed, including but not limited to a photodiode or an avalanche photodiode.

In certain embodiments, the processing unit 24 may be a personal desk top computer including all the acquisition and sort electronics 40 required for operating the sort head 50 and the separator 34 in response to signals produced by the detectors 128, 130. In another embodiment, the processing unit 24 may comprise a lap top with an external PCIe interface to the bus. An exemplary desk top PC may run a 32 bit operating system, such as Windows XP, or more a recent Windows operating system, and may include a dual core processor and have at least 256 MB of RAM. The acquisition and sort electronics 40 may be implemented on a PCIe board 44 having a programmable processor. The programmable processor may be a field programmable gate array 26, such as the Spartan 3A, available from XILINX, San Jose, Calif. US. Other field programmable gate arrays consisting of multiple thousands of configurable logic blocks may also be used. A field programmable gate array 26 may be desirable having configurable logic blocks which may operate asynchronously with a master clock. A field programmable gate array may further be desirable having configurable logic blocks with distributed RAM memory and without distributed RAM memory.

In combination with an amplifier unit 112, the processing unit 24 comprises a digital upgrade for some flow cytometer systems capable of replacing large racks including analog electronics. Specifically, the rack from an analog MoFlo™ (Beckman Coulter, formerly available from Cytomation) flow cytometer can be replaced with an amplifier unit 112 and a desk top computer having a PCIe board 44 with the field programmable gate array 26 (FPGA) described herein. The PCIe board 44 should be understood to include boards or cards having a PCIe interface 46.

The acquisition and sort electronics 40 or the PCIe board 44 may be connected through a common bus 48 in the desk top computer for displaying univariate histograms, bivariate plots and other graphical representations of acquired signals on a display for a graphical user interface 94 (GUI). Input devices may be associated with the GUI 94 such as a monitor, a touch screen monitor, a keyboard, or a mouse for controlling various aspects of the sort head 50 or separator 34.

As will be described in more detail below, the PCIe board 44 with the FPGA 26 may operate to identify the occurrence of a pulse 23 (seen in FIG. 5) in the signals produced by either the first detector 128 or the second detector 130 through the acquisition of signals and the execution of instructions on the PCIe board 44. Each detected pulse 23 may represent the presence of a particle 14 in the inspection zone 16 and may define an event, or a particle event. Generally, field programmable gate arrays contain thousands of programmable, interconnectable logic blocks. Embodiments of this disclosure comprise an FPGA performing parallel operations across programmed interconnected paths for performing one or more of the following functions: detecting pulses, calculating measured pulse parameters, translating measured pulse parameters; classifying particles; compiling event parameters; and making sort decisions. Programming architecture may be stored in individual configurable blocks or in combinations of configurable blocks, including configurable blocks with RAM and configurable blocks without RAM. Written instructions may be included on these configurable blocks and combinations of configurable blocks and may include bitmap look up tables (LUTs) state machines, and other programming architecture. In one aspect, written instructions stored on the FPGA may provide for constructing an event memory map tracking event parameters for each droplet, as well as tracking parameters for each event within each droplet.

The FPGA 26 may produce a number of control signals 116 to control the sort head 50. The control signals 116 may control operational parameters set by a user at the GUI 94 or may dynamically adjust parameters based on detected event parameters. The control signals 116 may include the drop drive signal 78 for controlling the oscillator 72 and a charge signal 92 for controlling the charge of the fluid stream 64 based upon a sort decision. The charge signal 92 is represented in FIG. 1 by the electrical connection for carrying the charge signal 92 from the processing unit 24 to an amplifier unit 112 and the electrical connection carrying the charge signal 92 from the amplifier unit 112 to a charge connection 126 in the nozzle assembly 62. The charge signal 92 carried from the amplifier unit 112 to a charge connection 126 in communication with the sheath fluid 56. An additional control signal 116 may include the strobe signal 120, represented by the electrical connection from the FPGA 26 to the amplifier unit 112, and from the amplifier unit 112 to the strobe 122.

Once a sort decision is determined for a particular particle 14, the fluid stream 64 may be charged with an appropriate charge just prior to the time a droplet 74 breaks off the fluid stream 64 encapsulating the particle 14. The droplet 74 may be subjected an electromagnetic field produced by the separator 34 for physically separating particles 14 based upon a desired characteristic. In the case of a jet-in-air flow cytometer, the separator 34 may comprise deflection plates 114. The deflection plates 114 may include high polar voltages for producing an electromagnetic field that acts on droplets 74 as they pass. The deflection plates 114 may be charged at up to ±3,000 Volts to deflect droplets 74 at high speeds into collection containers 126.

Figure 3:
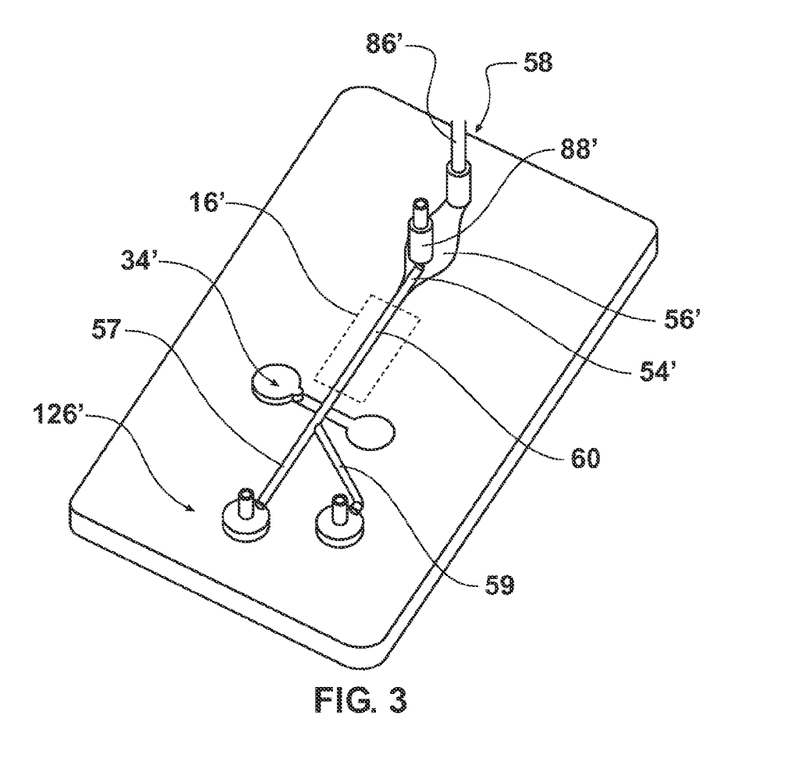
FIG. 3 illustrates an embodiment of a microfluidic chip in accordance with certain aspects of this disclosure.

Referring briefly to FIG. 3, an alternative particle delivery device 12' and separator 34' are depicted in the form of a microfluidic chip 58. The particle delivery device 12' may include a sample inlet 88' for introducing a sample 54 containing particles 14 into a fluid chamber 54' passing through an inspection zone 16'. The sample 54 may be insulated from interior channel walls and/or hydrodynamically focused with a sheath fluid 56 introduced through a sheath inlet 86'. After inspection at the inspection zone 16', with a measurement system, like the one described with respect to FIG. 1, particles 14 in the fluid chamber 54' can be mechanically directed to a first flow path 57 or a second flow path 59 with a separator 34', for altering fluid pressure or diverting fluid flow. The illustrated separator 34' comprises a membrane which, when depressed, may divert particles into the second flow path 59. Other mechanical or electro-mechanical switching means such as transducers and switches may also be used to divert particle flow.

PCIe Board Processing on a Field Programmable Gate Array

Figure 4:
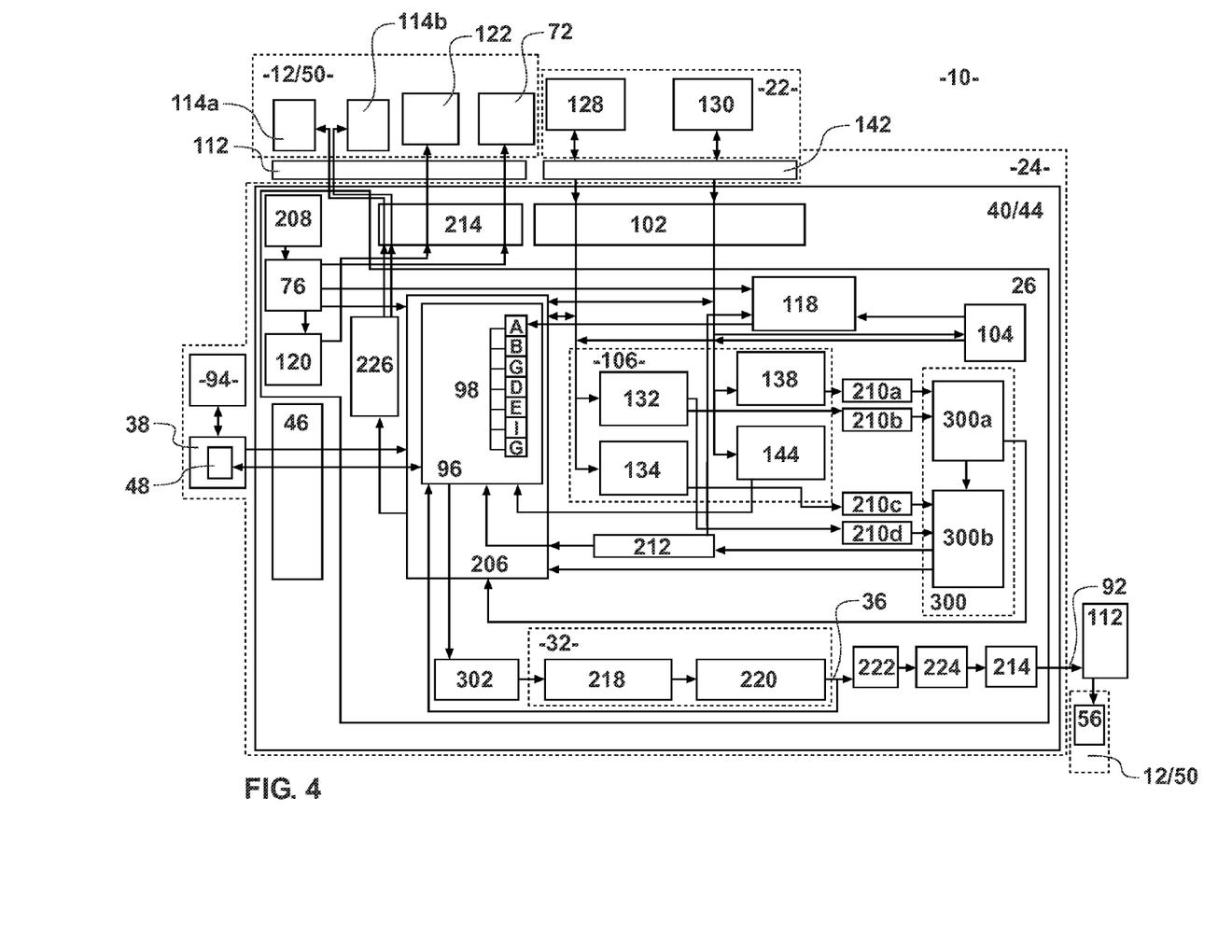
FIG. 4 illustrates a schematic of an embodiment of a flow cytometer including acquisition and sort electronics in accordance with certain aspects of this disclosure.

FIG. 4 provides a schematic representation of a particle sorting system 10, such as the system illustrated in FIG. 1. The particle sorting system 10 may include a detection system 22 in communication with a processing unit 24 for detecting and processing signals produced by particles 14 at the inspection zone 16. The processing unit 24 may include acquisition and sort electronics 40 and a Graphic User Interface (GUI) 94, for making particle classifications, making droplet sort decisions, displaying data, and modifying operating parameters of the particle delivery device 12.

FIG. 4 provides a focus on the processing unit 24, particularly, the acquisition and sort electronics 40 in the form of a PCIe board 44 including an FPGA 26. Physically, the FPGA 26 may comprise thousands of configurable logic blocks, input/output blocks, block RAM and master clock 208. For the purpose of FIG. 4 RAM 206 may represent both block RAM physically located at one location in the FPGA 26, as well as distributed RAM thorough the FPGA 26. Distributed RAM may include flip flops, shift registers and other software and hardware architecture for calling up stored variables. The configurable logic blocks may be individually programmed with written instructions for performing a number of logical functions or computations and may perform tasks individually or as collections of blocks. As illustrated in FIG. 4, the input/output blocks are omitted and some configurable logic blocks are grouped and characterized according to the functions they perform.

The detection system 22 provides signals from a first detector 128 and a second detector 130, which may be buffered and/or amplified by a detector preamplifier 142 and sampled by an analog to digital converter 102 (ADC) making 16 bit acquisitions from the signal at sample rates of 105 MSPS. Exemplary ADC converters are available from Analog Devices Inc. Once digitized, the signals may be processed by the FPGA 26 with specific instructions for detecting the presence of a pulse 23, sometimes referred to as an event or a particle event, calculating measured pulse parameters for each event, classifying particles based upon the measured pulse parameters, determining event parameters relating to expected droplets, and applying a sort logic to droplets based upon the event parameters and particle classifications.

Depending on the particle size and the pressure of the sample fluid, particles 14 may take about 1.3 microseconds to pass through the inspection zone 16, resulting in 200 data acquisitions by the ADC 102. Expected droplets may have the equivalent of about 1500 acquisitions additionally depending on the drop drive frequency. Once a digital signal, such as a 16 bit parameter, is produced by the ADC 102 acquisition representing a raw fluorescence value from a PMT it may compared against a threshold 104 by a threshold comparator for the determination of a pulse 23, or a particle event. The threshold 104 may include a first threshold for determining the beginning of a pulse, or for determining the occurrence of a rising edge of a pulse 23. A second threshold may be employed for determining the falling edge, or the end of a pulse 23. The first and second thresholds may be identical values, or the first threshold may be a higher value than the second threshold. The raw fluorescence values and information regarding the peak may be stored on RAM within the FPGA 26 and recalled by groups of configurable logic blocks in parallel for further processing and for the determination of status bits associated with individual particles 14 as well as for droplets 100.

Figure 5:
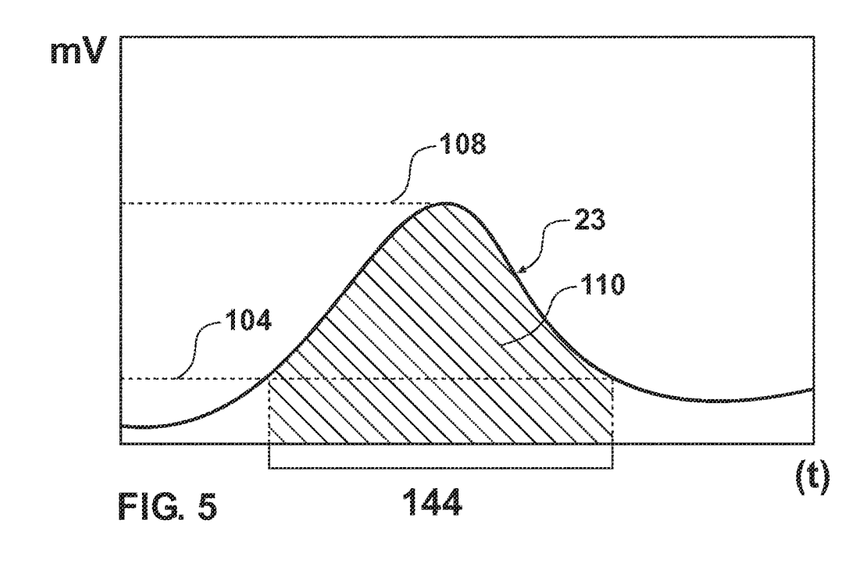
FIG. 5 illustrates an exemplary pulse representative of a particle passing through an inspection zone.

Referring briefly to FIG. 5, a pulse 23 representing a particle event is graphically illustrated as a detector signal in mV over time. The voltage may represent the amplified output of the first detector 128 or the second detector 130 and may encompass some measured pulse parameters that may be determined from these signals. The pulse peak 108 is illustrated as that peak signal value. The pulse duration 144, sometimes referred to as the pulse width, may represent the time over which the signal remains above the threshold 104, but may also be represented as the number of acquisitions above the threshold 104.

Turning back to FIG. 4, the FPGA 26 includes a group of configurable logic blocks with written instructions for determining measured pulse parameters 106 based upon the acquired signals. During the period in which the threshold 104 is exceeded, one set of configurable logic blocks may execute written instructions to perform the function of comparing each subsequent acquisition value with the previous highest value from the first detector (forward detector) to determine a forward pulse peak 132. Similarly, another set of configurable logic blocks may execute written instructions to perform the function of comparing each subsequent acquisition value with the previous highest value from the second detector (side detector) to determine a side pulse peak 138. Additional detectors with a variety of filters may be employed depending upon the particles of interest for compiling additional peak values from a variety of directions and/or at a variety of wavelengths.

Yet another group of configurable logic blocks within the measured pulse parameter 106 group may include instructions for adding each subsequent acquisition value for determining a pulse area. FIG. 4 illustrates a forward pulse area 134 determined from a forward signal from the first detector 128. A pulse duration 144 may be calculated from either detector and may represent the number of acquisitions above the threshold 104. Each of forward peak 132, side peak 138, forward area 134, and pulse duration 144 are non-limiting examples of measured pulse parameters 106 which may be calculated on the FPGA 26. Other values which may be calculated on the FPGA 26 based upon acquired detector signals may include extended window areas, reduced window areas, offset peaks, rise slopes, fall slopes, ratios thereof, and combinations thereof.

Based upon the FPGA 26 architecture, measured pulse parameters 106 may be calculated in parallel. Once a pulse 23, or particle event, has finished the measured pulse parameters 106 are immediately available for further processing, and the configurable logic gates are read to perform their mathematic operations on acquisitions from a new event.

Data acquired on the previous pulse may be manipulated on the FPGA 26 with a series of configurable logic gates. The manipulation may include elements for data rotation 210 to improve a user's ability to differentiate data. In one non-limiting embodiment, the data manipulation may include compensation for drift or other factors.

The manipulated data may further be processed with written instructions on the FPGA 26 for classifying particles. Configurable logic blocks may include written instructions for comparing the rotated data, or non-rotated data, against one or more bitmap look up tables 300 (LUTs). The LUTs (300) may be stored in RAM 206 or may be distributed amongst configurable logic blocks. In the illustrated example, a first LUT 300a may include forward peak and side peak fluorescence values for a determination as to whether or not particles are oriented. A second LUT 300b, may take input from the first LUT 300a as well as forward peak and forward area in order to distinguish other particle characteristics. In the case of sperm, first LUT 300a may differentiate oriented sperm from unoriented sperm and the second LUT 300b, may differentiate X chromosome bearing sperm from Y chromosome bearing sperm based upon differences DNA content. A classification element 212, which may include a configurable logic block, or a series of configurable logic blocks, characterized as a state machine may take the output from the LUTs 300 and assign a classification, or more than one classification to each event.

Based upon the bitmap LUTs 300, each event may be classified into several categories. In the event the pulse duration exceeds a threshold the event may be categorized as a multi-particle event. In the case of sperm, from the front and side detectors described, the events may be classified as, live sperm, dead sperm, oriented sperm, unoriented sperm, X-chromosome bearing sperm, Y-chromosome bearing sperm, other types of sperm, and combinations thereof. However, other configurations may also be implemented on the FPGA 26. Any number of detectors may be configured with any number of filters for detecting specified wavelengths of emitted or reflected electromagnetic radiation 20 as previously described. Similarly, any number of LUTs 300 may be configured to distinguishing a number of cell or particle characteristics.

A group of state machines may be implemented on the FPGA 26 to determine event parameters 118 for each droplet and for constructing an event memory map 96 in the RAM 206 of the FPGA 26. Event windows 98 may be created in the event memory map 96 with input from to a drop drive signal generator 76. The drop drive signal generator 76 may receive a clock signal from the master clock 208 and produce a user defined waveform at a desired frequency as an output. The drop drive signal may be provided through a digital to analog converter 214 (DAC) and then to the oscillator 72 for perturbing the fluid stream 64 into droplets 74. The DAC 214 may be capable of sampling 16 bit digital data at 50 MSPS for producing analog signals. The DAC 214 may provide analog signals to the sort head for controlling additional sort operations, such as for operating the deflection plates 114 and charging the fluid stream 64. As an input to the event memory map 96, the drop drive signal generator 76 may provide a precise indication of the expected leading end of a droplet and tail end of a droplet 74. Event parameters 118, including particle classification 212, may be associated by the event memory map 96 to specific event windows 98(a-g), which may correspond to expected droplets 100(a-g) (seen in FIG. 1).

Additional event parameters 118 may be determined from the measured pulse parameters 106, the particle classification 212, the threshold 104 and the drop drive signal generator 76. For example, the number of particles in an expected droplet 100 can be determined by the number of times the threshold 104 is exceeded in an event window 98. Similarly, the timing at which the threshold 104 is exceeded, with reference to the drop drive signal generator 76, may provide an indication of the locations particles 14 in each droplet 74. Each of the determined event parameters 118 may be determined in parallel by groups of configurable logic blocks and stored as status bits in RAM 206. The status bits may then be compiled into the event memory map 96, or may be further process to derive variables or other status bits for the event memory map 96.

A state record 302 may be compiled by state machines based upon information in the event memory map 96. The state record 302 may be applied to several sets of state machines having written instructions for making a sort decision 32. These instructions may also be referred to as a sort logic 32 and are utilized to arrive at a sort decision 36. The state record 302 can include the relevant event parameters 118 for each event in a droplet of interest. Additionally, the state record 302 may include relevant event parameters 118 for the droplet of interest, as well as for the previous droplet and the next droplet. FIG. 4 illustrates a first set of state machines 218 for making a sort decision based upon events with the current droplet. As one example, the first set of state machines 218 may be capable of processing a state record 302 having classification and other relevant information on up to six particles. The first set of state machines 218 may provide instructions relating to statistical decisions relating to the desired purity and the expected purity of a sort sample based on the current droplet. The second set of state machines 220 may provide written instructions relating to the locations of particles in droplets and to the status of the previous droplet as well as the status of the next droplet. Once a sort decision 36 is reached from the sort logic 32, it may be applied to series of sort sequence state machines 222 which consider the previous charges applied in order to produce a signal representative of the correct voltage amplitude to apply for the current sort charge signal 92. As but one non-limiting example, in the instance consecutive droplets charged for the same sort path, each particle may require 20% more voltage than the previous.

Finally, a drop delay 224 may be applied to the signal representative of the charge signal 92. The charge signal 92 can then be passed through the DAC 214 to the amplifier unit 112 and then to the sort head 50 for charging the sheath fluid 56 to perform the desired sort.

In addition to the charge signal 92 and the oscillator 72, the FPGA 26 may include written instructions for controlling the strobe 122 and the deflection plates 114a, 114b. The strobe signal 120 may be generated with written instructions on a series of interconnected configurable logic blocks in the FPGA 26 based upon the drop drive signal generator 76. For example, the strobe signal may be produced from the drop drive signal with a 10% duty cycle.

The FPGA 26 may also include a set of high voltage state machines 226 for producing a signal representing whether the deflection plates should be off or on. This signal may be passed through the DAC 214 then the amplifier unit 112 to provide each deflection plate 114a, 114b with a high voltage.

Settings for the drop delay, drop drive signal generator, strobe, high voltage, as well as modifications to the LUTs 300, and the sort logic may be applied to the FPGA 26 through the GUI 94 on a computer 38 sharing a common bus 48 with the PCIe board having the FPGA 26. The common bus 48 may interface the PCIe board 44 through a PCIe interface 46. The PCIe interface 46 may provide for data transfer at a rate of 180 mebytes per second. Data streamed through the PCIe interface 46 to the GUI 94 can include event rates, abort rates, total sorted particles, rotate or non-rotated plots generated from measured pulse parameters and other variables.

Figure 6:
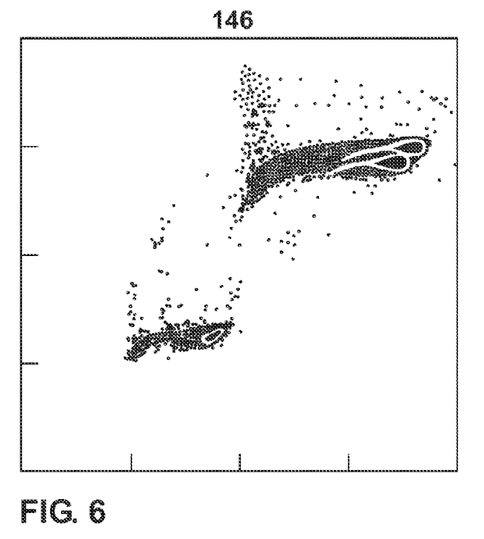
FIG. 6 illustrates a univariate plot of measured pulse parameters in accordance certain aspects of this present disclosure.

FIG. 6 represents a bivariate histogram 146, such as one that may be displayed by a monitor or a touch screen of the GUI 94 demonstrating a forward peak fluorescence on one axis and a side peak fluorescence on the other axis. In some aspects of the present disclosure the bivariate data may be rotated with instructions stored on the FPGA 26. Prior to communication to the graphic user interface through the PCIe interface 46. The rotation can be achieved by user input in response to a current bivariate plot 146.

Figure 7:
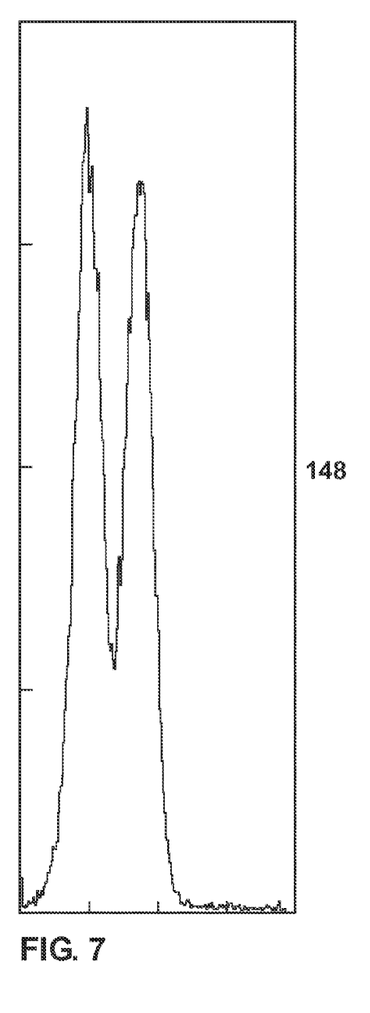
FIG. 7 illustrates a bivariate plot in accordance with certain aspects of this disclosure.

FIG. 7 represents a univariate histogram 148 which may form part of the graphical display associated with a sorting process. As a non-limiting example the univariate histogram could illustrate a count of particles having certain peak intensities or areas. The univariate histogram 148 may provide visual feed back for a user regarding a coefficient of variation. A user may adjust operational parameters, or instructions may be stored on the FPGA or the computer with the GUI 94 for adjusting operational parameters to achieve a desired coefficient of variation.

Event Memory Map

In operation, a particle sorting system 10, as substantially described in FIG. 1 may provide a fluid stream 64 containing a plurality of particles 14. Each particle 14 represents an event producing a pulse 23 of emitted or reflected electromagnetic radiation 20 at the inspection zone 16. The pulse 23 may detected by the detection system 22 and converted to a digital signal by the processing unit 24.

At the processing unit 24, an event memory map 96 may be generated in the RAM 206 of the FPGA 26. The event memory map 96 may be partitioned into event windows 98(a-g) with input from the drop drive signal generator 78 to provide an accurate representation of the timing between droplets. The event windows 98 may be capable of storing information relating to between one and six particles. In one embodiment, the event windows 98(a-g) may include information on as many as twelve particles expected within a single droplet. In addition to the drop drive signal, a drop delay must be determined to ensure event windows 98(a-g) (FIG. 4) correspond precisely to expected droplets 100(a-g) (FIG. 1). In an embodiment where the drop delay is dynamically varied, the user defined of calibrated drop delay may be referred to as the initial drop delay.

Within an expected droplet 100, each pulse 23 may represent a particle 14. Each pulse 23 may be processed for measured pulse parameters 106, previously described, and may associate one or more status bits with each particle. The first status bit may relate to the existence of an event determined when a pulse 23 exceeds the threshold 104. Additional status bits may be determined, such as the classification of a particle, whether or not a pulse duration threshold was exceeded indicating more than one particle stuck together, and other information about the particles. The classifications determined from the measured pulse parameters 106 may be stored in the event memory map 96 in the associated event window 98 for the classified particle. Classifications may be sorted in the form of status bits, which may be a 8-bit, 16-bit, 32-bit, 64-bit, or 128-bit words. Optionally, other parameters and measured pulse parameters 106 may independently be determined in parallel and then compiled in the event memory map 96. In this way, the capacity of a field programmable gate array 26 may be fully utilized with asynchronous operations performed on related or independent groups of configurable logic gates thereby providing an efficient and robust methodology for tracking parameters associated with each individual event, as well as parameters associated with each droplet.

In addition to information specific to individual events, the event memory map 96 may be populated with event parameters 118 associated with the expected droplets 100, regardless of whether or not the droplets 100 contain particles 14. As one example, the timing of a pulse start may be cross referenced with the drop drive signal in order to derive the location of the particle 14 in the expected droplet 100. In this way, precise determinations of the particle 14 location can be determined. These event parameters 118 may be determined by groups of configurable logic blocks which in turn produce status bits that may be stored on the event memory map 96.

For the example of particle location, a status bit may be produced when a particle is too close to the droplet leading end or to close to the droplet tail end. Similarly, status bit may be produced as 8-bit, 16-bit, 32-bit, 64-bit, or 128-bit words for any of the other event parameters 118 determined on the FPGA 26.

As another example, an event parameter 118 may include a status bits indicating whether each event in an expected droplet has the same classification or not. This status bit could be utilized in a purity mode sort to arrive at a sort decision. In other sorting modes the numbers of each classification of particle in an expected droplet may be compared against a bitmap or a LUT or another statistical procedure may be employed.

The various status bits representing event parameters 118 in the event memory map 96, may be compiled into a state record 302 which may contain only those parameters relevant to making specific sort decisions. The state record 302 may then be applied as an input to groups of configurable logic gates operating as state machines for applying a sort logic 32 to make a sort decision 36.

The sort decision 36 itself may be stored as a status bit for determinations relating to the next and the previous droplets. For example, different charges are required in subsequent droplets to achieve the same sort path.

Dynamic Sorting

Settings and other operational parameters may also be dynamically varied independent of input from the user at the GUI 94. Operational parameters may include input parameters dictating the operation of a flow cytometer including, but not limited to, drop drive frequency, drop drive amplitude, drop drive waveform, drop phase, drop delay, charge signal amplitude, charge signal duration, sample flow rate, sample flow pressure, sheath flow rate, sheath flow pressure. Additionally, operations parameters may relate to output parameters such as, but not limited to, event rates, abort rates, sort rates, total sorted particles, and sort purities. In one aspect, the event memory map 96 may provide a means for making dynamic adjustments to the particle sorting system 10. Data from the event memory map 96 can be sampled periodically for the purpose of periodically adjusting various parameters associated with sorting. The determination to change sort parameters can be based upon desired throughout, desired purity, system performance, a coefficient of variation, or other parameters. For example, sample pressure and/or sheath pressure may be adjusted to improve throughput or purity on a periodic basis. Other parameters, such as the drop delay may be modified for specific droplets on an individual basis based upon information on the event memory map such as the location of an event within a droplet.

As a non-limiting example, some cells, particularly sperm cells having tails, can actually affect the surface tension properties of forming droplets and change the precisely calibrated drop delay when located at the tail edge of an expected droplet. The time at which a charge is applied to the forming droplet is precisely tied to the drop delay in order to ensure each droplet receives the correct charge. Since flow cytometers form droplets for most sorting functions at frequencies in the range of 20 kHz to 100 kHz, extremely small changes to the drop delay can result in errors applying a charge to an intended droplet. Even if the drop delay is out of phase by a small fraction droplets may not receive the full charge they were intended to receive and droplets that should be neutral may receive a small charge and towards maintaining a good quality/narrow stream. This can exacerbate the phenomenon of fanning which relates to induced charges on droplets that were intended to remain neutral.

Therefore, a need exists for a device and method for precisely tracking the location of particles within expected droplets and dynamically modifying the drop delay when the particle location is expected to alter the drop delay at which the droplet detaches from the fluid stream.

Certain embodiments may provide a method and system for determining dynamically varying a drop delay and may begin with the step of determining an initial drop delay in a jet-in-air flow cytometer. The initial drop delay may be determined in a calibration step of flow cytometry. The initial drop delay calibration may begin with a coarse calibration for determining the number of periods required for a droplet to form. The coarse determination can be followed by a fine determination representing a fraction of a period. The fractions may be in terms of $\frac{1}{20}$ or $\frac{1}{32}$ of a period. Depending on the drop drive frequency, fractions may be indicated on the FPGA in increments as small as $\frac{1}{1000}$ of the drop period.

Sperm, for example, may have tails which extend the length nucleus by two to four times, or more, depending on the species. Based on the size of the droplets there is an increase chance the tails may extend through the end of a forming droplet, and in doing so they may affect local surface tension properties and change the predicted break off point of the droplet. Stains used in many applications, such as sex sorting, selectively bind to nuclear DNA. Therefore, based upon only the signals produced by a detection system it may be difficult to distinguish if sperm have ended up in a tail first alignment. Therefore, it may be desirable to decrease the drop delay when sperm are located at the leading end as well. When sperm are located right on the leading end of a droplet it may also be desirable to decrease the drop delay of the previous droplet.

As one specific example, in the instance of sperm, the drop delay may be slightly extended when an event threshold is crossed in the last quarter of a droplet. Similarly, the drop delay may be decreased for sperm located in the first quarter of the droplet. The front threshold may also be modified when a threshold is crossed in a much smaller window, such as in the first $\frac{1}{20}$, or in the first $\frac{1}{1000}$ of the droplet.

Particles may be detected and analyzed by various detection systems for differentiating particle characteristics in order to provide a sort decision for each droplet. In addition to the sort decision, the location of each particle in a droplet may be determined in a manner previously discussed, or by another similar methodology.

FPGA Sort and Acquisition Sorting

Staining—Sperm was diluted to about $160 \times 10^6$ sperm per ml in a modified TALP buffer known for sorting sperm and described in U.S. Pat. No. 7,208,265 Table 3, at a pH of 7.4. Samples collected from bovine were incubated with Hoechst 33342 for between 45 and 60 minutes at 34° C. After incubation an equal volume of a second modified TALP was added reducing the concentration to about $80 \times 10^6$. The second modified TALP includes the same components as the first modified TALP with the addition of 4% egg yolk, 40 mM red food dye No. 40 (20 g/L) and the pH was dropped to 5.5 with HCl. The sample was divided into two portions.

Sorting—Just prior to sorting, each sample was filtered though a 40 µm nylon mesh. The first portion of the sample was sorted on a MoFlo SX (Beckman Coulter, Inc., CA USA) at 40 psi. The combination of the trigger rate and the coincident rate (collective the effective event rate) was maintained at 42,500 per second and sorted for X-chromosome bearing sperm. After the first portion of sample was sorted, the analog acquisition and sort electronics were replaced with a personal computer having a PCIe board with an FPGA processor programmed for sorting sperm. The MoFlo amplifier was also replaced with an amplifier unit for providing signals to the sort head. The modifications took about an hour. The second portion of the same sample was then sorted on the same sort head with the new acquisition and sort electronics at a pressure of 40 psi and at an event rate of about 41,000 per seconds. For both sorts, the sort headed oriented about 60% of the sperm while about 10% of the sperm were dead.

Results—The first portion of sample was sorted effectively at an event rate of 42,500 events per second. Of those events 6,800 per second were coincident, or too close to process, with an additional 2000 per second aborted due to sort logic resulting in 5,100 X-chromosome bearing sperm sorted per second. The second portion of the sample was sorted at an event rate of 41,000 per second. Of the 41,000 events per second 3,400 were aborted due to sort logic, while coincidences, or events too close to process, were eliminated allowing a sort rate of 6,300 X-chromosome bearing sperm per second. Both sorts provided for collected samples at about 91% purity, while the FPGA acquisition and sort electronics demonstrated about a 23.5% increase in the sort rate at comparable event rates.

As can be easily understood from the foregoing, the basic concepts of the present invention may be embodied in a variety of ways. The invention involves numerous and varied embodiments of flow cytometry acquisition and sort electronics and methods including, but not limited to, the best mode of the invention.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity; for example, "a container" refers to one or more of the containers. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

Thus, the applicant(s) should be understood to claim at least: i) a flow cytometer with acquisition and sort electronics herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, and x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A method of sorting particles comprising the steps of:
delivering a fluid stream containing particles to an inspection zone and interrogating the particles at the inspection zone with a source of electromagnetic radiation wherein interrogated particles produce emitted or reflected electromagnetic radiation;
detecting the emitted or reflected electromagnetic radiation of the interrogated particles and producing at least one signal containing at least one pulse representative of at least one interrogated particle characteristic;
comparing the at least one signal to a trigger threshold to determine the occurrence of a particle event;
generating an event memory map having event windows, each of the event windows associated with an expected sortable unit of the fluid stream;
coordinating each particle event to one of the event windows in the event memory map;
determining measured pulse parameters for each particle event from the at least one signal;
classifying particles based upon the measured pulse parameters;
determining event parameters for each of the event windows;
applying a sort logic to make a sort decision based on the event parameters and particle classifications associated with each of the event windows;
sorting particles within each of the event windows according to the respective sort decisions; and
collecting at least one population of sorted particles.

2. The method according to claim 1 wherein the step of generating at least one signal containing at least one pulse representative of the at least one interrogated particle characteristic further comprises the steps of:
generating a first signal based upon the emitted or reflected electromagnetic radiation produced by excited particles at the inspection zone in a first direction; and
generating a second signal based upon the emitted or reflected electromagnetic radiation produced by excited particles at the inspection zone in a second direction.

3. The method according to claim 1 wherein the step of coordinating each particle event to one of the event windows in the event memory map further comprises the step of comparing the time stamp of the particle event to a time associated with the event window in the event memory map.

4. The method according to claim 1 wherein an event parameter for each of the event windows corresponds to an amount of time representing sortable units.

5. The method according to claim 1 wherein the sortable units comprise expected droplets.

6. The method according to claim 5 further comprising the steps of:
forming the fluid stream into droplets downstream of the inspection zone;
charging the droplets according to their associated sort decision; and
deflecting charged droplets into collection receptacles.

7. The method according to claim 6 wherein the step of forming droplets further comprises applying a drop drive signal to an oscillator for forming the fluid stream into droplets.

8. The method according to claim 7 wherein the event windows of the event memory map are generated in response to the drop drive signal.

9. The method according claim 1 further comprising the step of recording the sort decision in the event memory map for each of the event windows.

10. The method according to claim 9 further comprising the step of recording the event parameters resulting in a particle in one of the event windows not being sorted.

11. The method according claim 1 wherein the event parameters are selected from the following: droplet number, droplet time stamp, number of particle events in a droplet; sort results, light scatter, light extinction, fluorescence, event duration, event start time, location of a particle in a droplet, particle classifications and combinations thereof.

12. The method according claim 1 wherein the measured pulse parameters are selected from the group consisting of: forward pulse peak, side pulse peak, forward pulse area, side pulse area, forward pulse slope, side pulse slope, pulse duration, and combinations thereof.

13. The method according to claim 1 wherein the particles comprise sperm cells and wherein the particle classification comprises classifications selected from the group consisting of: X-chromosome bearing sperm; Y-chromosome bearing sperm; oriented sperm; unoriented sperm; live sperm; dead sperm, and combinations thereof.

14. The method according to claim 1 wherein the steps of comparing the at least one signal to a trigger threshold to determine the occurrence of a particle event, coordinating each particle event to one of the event windows in the event memory map, determining measured pulse parameters for each particle event, and classifying particles based upon the measured pulse parameters are performed on a field programmable gate array.

15. The method according to claim 1 wherein the step of classifying particles based upon the measured pulse parameters further comprises the step of comparing measured pulse parameters to a bitmap in the form of a look up table.

16. The method according to claim 1 further comprising the step of generating a state record from the event memory map.

17. The method according to claim 16 wherein the state record comprises the information required for making a sort decision.

18. The method according to claim 1 wherein information stored in the event memory map is applied in a sort logic to subsequent particles.

19. The method according to claim 18 further comprising the step of comparing particle classifications within a single one of the event windows.

20. The method according to claim 19 further comprising the step of modifying the sort decision for event windows having more than one classification of particles based upon a projected purity of the collected population of sorted particles.

21. The method according to claim 1 wherein the particles comprise sperm cells.

22. The method according to claim 21 wherein measured pulse parameters are compared against a bitmap look up table to classify a subpopulation of sperm cells as oriented live sperm cells.

23. The method according to claim 22 wherein measured pulse parameters are compared against a bitmap look up table to classify a sperm cells as X chromosome bearing sperm cells or Y chromosome hearing sperm cells.

24. The method according to claim 23 wherein only sperm cells classified as live oriented sperm cells are further classified as X chromosome bearing or Y chromosome bearing sperm cells.

25. The method according to claim 1 further comprising the step of detecting from the event memory expected changes in operational parameters.

26. The method according to claim 25 further comprising the step of applying a compensation when expected changes in operational parameters are detected from information contained in the event memory map.

27. The method according to claim 26 wherein the operational parameters comprises a sort delay and wherein the step of applying a compensation when expected changes in operational parameters are detected further comprises changing the sort delay when a particle is detected at the tail end of an expected sortable unit.

28. The method according to claim 26 wherein the step of applying a compensation further comprises modifying the sort delay for individual expected sortable units.

29. The method according to claim 26 wherein the sort delay is increased for an expected sortable unit with a particle located at tail end of the unit.

30. The method according to claim 26 wherein the sort drop delay is decreased for an expected sortable unit with a particle located at the leading end of the unit.

* * * * *